(12) United States Patent
Davis et al.

(10) Patent No.: US 11,963,704 B2
(45) Date of Patent: Apr. 23, 2024

(54) SURGICAL INSTRUMENT AND METHOD

(71) Applicant: Warsaw Orthopedic, Inc., Warsaw, IN (US)

(72) Inventors: Darren L. Davis, Knoxville, TN (US); Amanda D. Tong, Memphis, TN (US); Cristian A. Capote, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 216 days.

(21) Appl. No.: 17/476,963

(22) Filed: Sep. 16, 2021

(65) Prior Publication Data
US 2023/0078790 A1    Mar. 16, 2023

(51) Int. Cl.
*A61B 17/70* (2006.01)
*A61B 17/00* (2006.01)
*A61B 17/80* (2006.01)

(52) U.S. Cl.
CPC ...... *A61B 17/808* (2013.01); *A61B 17/00234* (2013.01); *A61B 2017/00336* (2013.01); *A61B 2017/00367* (2013.01)

(58) Field of Classification Search
CPC ........ A61B 17/808; A61B 2107/00367; A61B 17/7074; A61B 17/8872; A61B 17/8858
USPC ...................................................... 606/86 B
See application file for complete search history.

(56) References Cited

U.S. PATENT DOCUMENTS

| | | | |
|---|---|---|---|
| 8,246,660 B2 | 8/2012 | Boris et al. | |
| 8,425,520 B2 | 4/2013 | Zalenski et al. | |
| 8,562,681 B2 | 10/2013 | Shepard et al. | |
| 9,055,982 B2 | 6/2015 | Chind | |
| 9,968,380 B2 * | 5/2018 | Robinson | A61B 17/7059 |
| 10,039,646 B2 | 8/2018 | Shepard et al. | |
| 10,105,234 B2 | 10/2018 | Squires et al. | |
| 10,695,107 B2 * | 6/2020 | Squires | A61B 17/862 |
| 2010/0106196 A1 * | 4/2010 | Erickson | A61B 17/1728 606/281 |
| 2015/0257789 A1 * | 9/2015 | Squires | A61B 17/7071 606/246 |
| 2016/0354126 A1 | 12/2016 | Nayet et al. | |

* cited by examiner

*Primary Examiner* — Nicholas J Plionis
*Assistant Examiner* — Christina Negrellirodriguez
(74) *Attorney, Agent, or Firm* — Sorell, Lenna & Schmidt, LLP

(57) ABSTRACT

A surgical instrument includes a first member defining an axis and a second member having at least one capture element. The at least one capture element being axially translatable relative to the first member such that the at least one capture element is outwardly radially movable relative to the axis and inwardly radially movable relative to the axis to capture a spinal plate. Systems, implants and methods are disclosed.

20 Claims, 18 Drawing Sheets

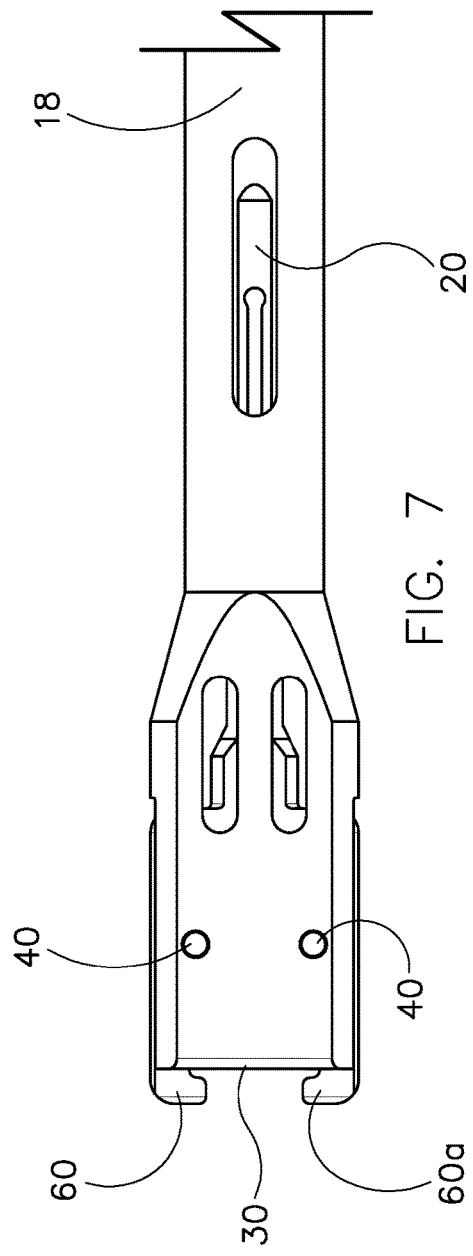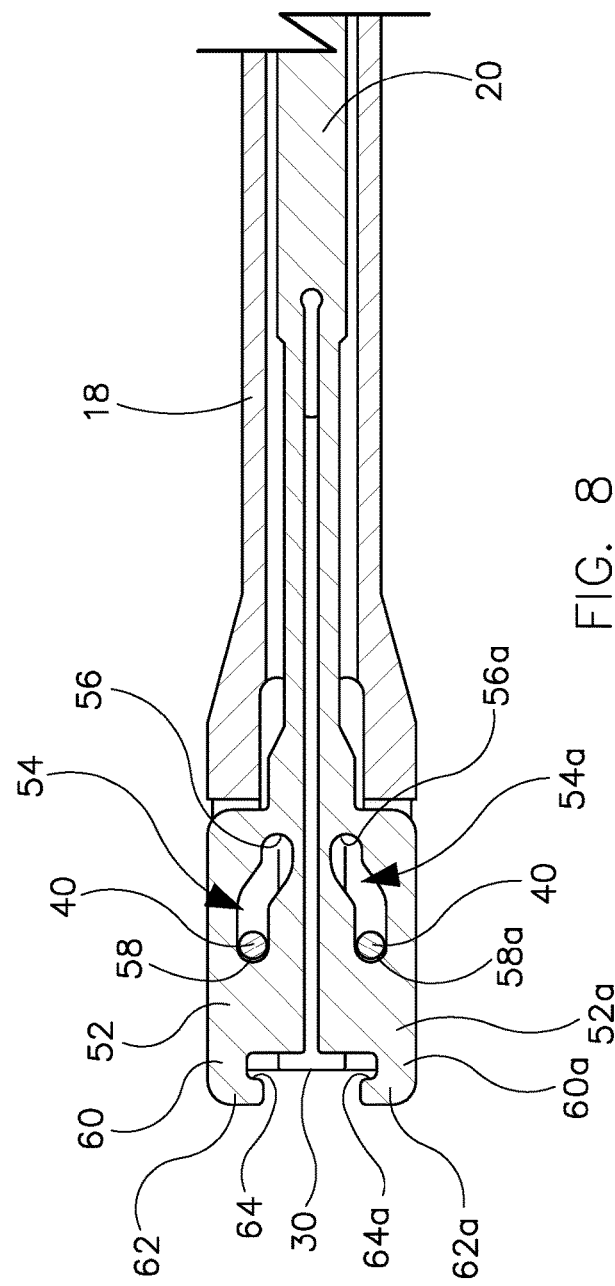

SURGICAL INSTRUMENT AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, implants such as bone fasteners, plates, connectors and vertebral rods are often used to provide stability to a treated region. These implants can redirect stresses away from a damaged or defective region while healing takes place to restore proper alignment and generally support the vertebral members. For example, plates may be attached via the fasteners to the exterior of one or more vertebral members. This disclosure describes an improvement over these technologies.

SUMMARY

In one embodiment, a surgical instrument is provided. The surgical instrument comprises a first member defining an axis and a second member having at least one capture element. The at least one capture element being axially translatable relative to the first member such that the at least one capture element is outwardly radially movable relative to the axis and inwardly radially movable relative to the axis to capture a spinal plate. In some embodiments, systems, implants and methods are provided.

In one embodiment, the surgical instrument includes an outer tube defining an axis and a center shaft having a pair of tangs. The pair of tangs being axially translatable relative to the center shaft such that the pair of tangs are outwardly radially movable relative to the axis and the pair of tangs are inwardly radially movable relative to the axis to capture a lamina plate.

In one embodiment, the surgical instrument includes a first member defining an axis and a second member including a capture member being axially translatable relative to the first member. The capture member is expandable and contractible for capturing a spinal plate.

BRIEF DESCRIPTION OF THE DRAWINGS

The present disclosure will become more readily apparent from the specific description accompanied by the following drawings, in which:

FIG. 7 is a break away view of components shown in FIG. 1;

FIG. 8 is a break away cross sectional view of components shown in FIG. 7;

DETAILED DESCRIPTION

Figure 1:
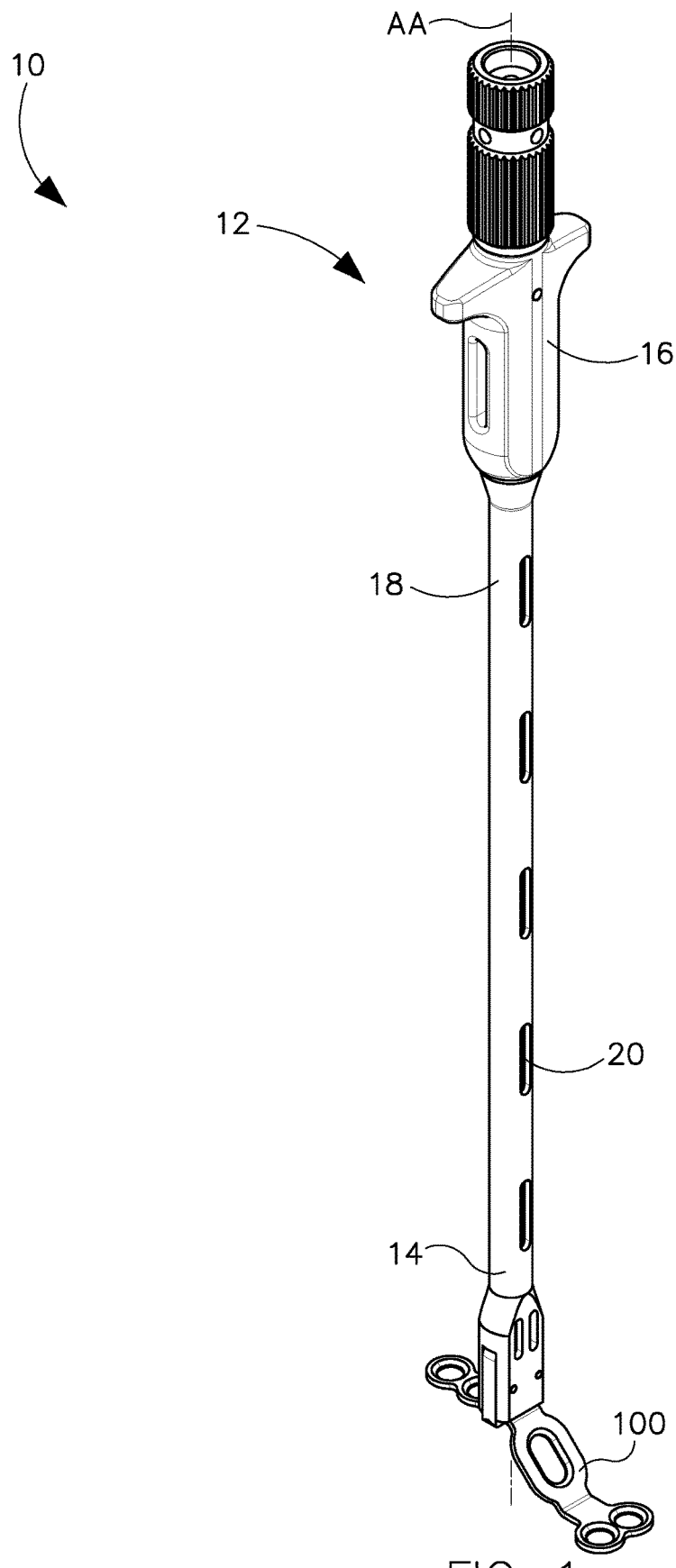
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine.

In some embodiments, the surgical system includes a surgical instrument, for example, a plate holder. In some embodiments, the plate holder is configured for engagement with spinal plates. In some embodiments, the spinal plates include cervical and/or lamina plates. In some embodiments, the plate holder includes a plate attachment mechanism configured to engage with a plate such that the plate is provisionally secured to the plate holder. In some embodiments, a footprint of the plate holder is reduced to improve visibility during a procedure.

In some embodiments, the present surgical system includes a plate holder configured for use in a laminoplasty procedure that includes removing a portion of vertebral tissue, for example, a portion of a spinous process and/or lamina and placing an implant, for example, a plate adjacent and/or between the tissue adjacent a vertebra to form a bridge. In some embodiments, the laminoplasty is a cervical laminoplasty. In some embodiments, the laminoplasty is implemented to provide spinal decompression for spinal neuroforaminal narrowing. In some embodiments, cervical laminoplasty provides spinal cord decompression for multilevel cervical myelopathy, multi-segmental spondylosis, and/or ossification of the posterior longitudinal ligament (OPLL). In some embodiments, during a laminoplasty, a portion of vertebral tissue is removed, including thinning lamina overlying the spinal cord on a side while cutting a second side of the lamina all of the way through to create a hinge on one side of the lamina and a small opening on the other side of the lamina. In some embodiments, the lamina is hinged opened. In some embodiments, failed laminoplasties occur via restenosis due to hinge closure. In some embodiments, current techniques have been applied to maintain an open hinge while a patient heals the laminar hinge in an expanded position. In some embodiments, plates and screws are implemented in a laminoplasty to facilitate patient rehabilitation and can increase preservation of motion in the patient.

In some embodiments, the present surgical system includes a plate holder. In some embodiments, a plate is provisionally secured to the plate holder. In some embodiments, the plate attaches to the plate holder more securely relative to existing plate holders. In some embodiments, the plate holder is configured to facilitate plate manipulation within the surgical site. In some embodiments, the plate holder includes a low profile relative to existing plate holders to improve visibility during a procedure. In some embodiments, a user can implement the plate holder with a single hand. In some embodiments, the plate holder can be advanced and retracted via an actuator operated by a user's thumb.

In some embodiments, the present surgical system includes a plate holder configured to position a plate, for example, a lamina plate within a section of a spine. In some embodiments, the lamina plate is positioned between a lateral mass and lamina for stabilization of anatomical structures protecting the spinal cord.

In some embodiments, the present surgical system includes a plate holder having a tip configured for engagement with a plate. In some embodiments, the tip is disposed at a distal end of an outer tube and a center shaft of the plate holder. In some embodiments, the plate holder includes a straight tip. In some embodiments, the plate holder includes an angled tip. In some embodiments, the straight or angled tip is configured to engage a plate at varying orientations on the plate. In some embodiments, an attachment angle differs between the plate and plate holder depending on the type of plate, for example, a lamina plate being positioned within an anatomy of a patient. In some embodiments, the plate holder attaches to the plate at 45 degrees. In some embodiments, engagement of the plate holder and the plate is dependent on a center shaft orientation relative to patient anatomy. In some embodiments, the plate holder attaches to the plate at a center of the plate.

In some embodiments the present surgical system includes a plate holder having a center shaft, an outer tube, a retaining clip, a tee handle, a tee handle pin, a pair of splay pins, a pair of spring caps, a spring, a turn knob and/or a knob retaining clip. In some embodiments, the center shaft is defaulted to a retracted position due to force of the spring on the center shaft. In some embodiments, when the turn knob is unthreaded from a proximal end of the plate holder, the turn knob is gapped off a proximal end of a tee handle, allowing the turn knob to function as a push button to extend a pair of center shaft tangs disposed at the tip. In some embodiments, when the pair of tangs are extended, a pair of splay pins track within distal slots located within a center of the pair of tangs. In some embodiments, the pair of tangs are opened to facilitate capture of the plate. In some embodiments, release of the push knob provisionally secures the plate with the pair of tangs. In some embodiments, the plate is captured and the knob can be fully tightened to mechanically compress and lock the plate to the plate holder.

In one embodiment, one or all of the components of the surgical system are disposable, peel-pack, pre-packed sterile devices used with an implant. One or all of the components of the surgical system may be reusable. The surgical system may be configured as a kit with multiple sized and configured components. In one embodiment, the surgical system includes one or a plurality of guides, each guide be configured for disposal with a plate at a different angle.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-13, there are illustrated components of a surgical system 10, including a surgical instrument, for example, a plate holder 12, as shown in FIG. 1.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

The components of surgical system 10 including plate holder 12 are employed, for example, with a minimally invasive procedure, including percutaneous techniques, mini-open and open surgical techniques to deliver and introduce an implant, such as, for example, one or a plurality of bone fasteners and/or spinal plates, at a surgical site within a body of a patient, for example, a section of a spine. In some embodiments, surgical system 10 can be employed, for example, in laminoplasty procedures to treat patients suffering from a spinal disorder to provide stabilization and decompression.

Figure 3:
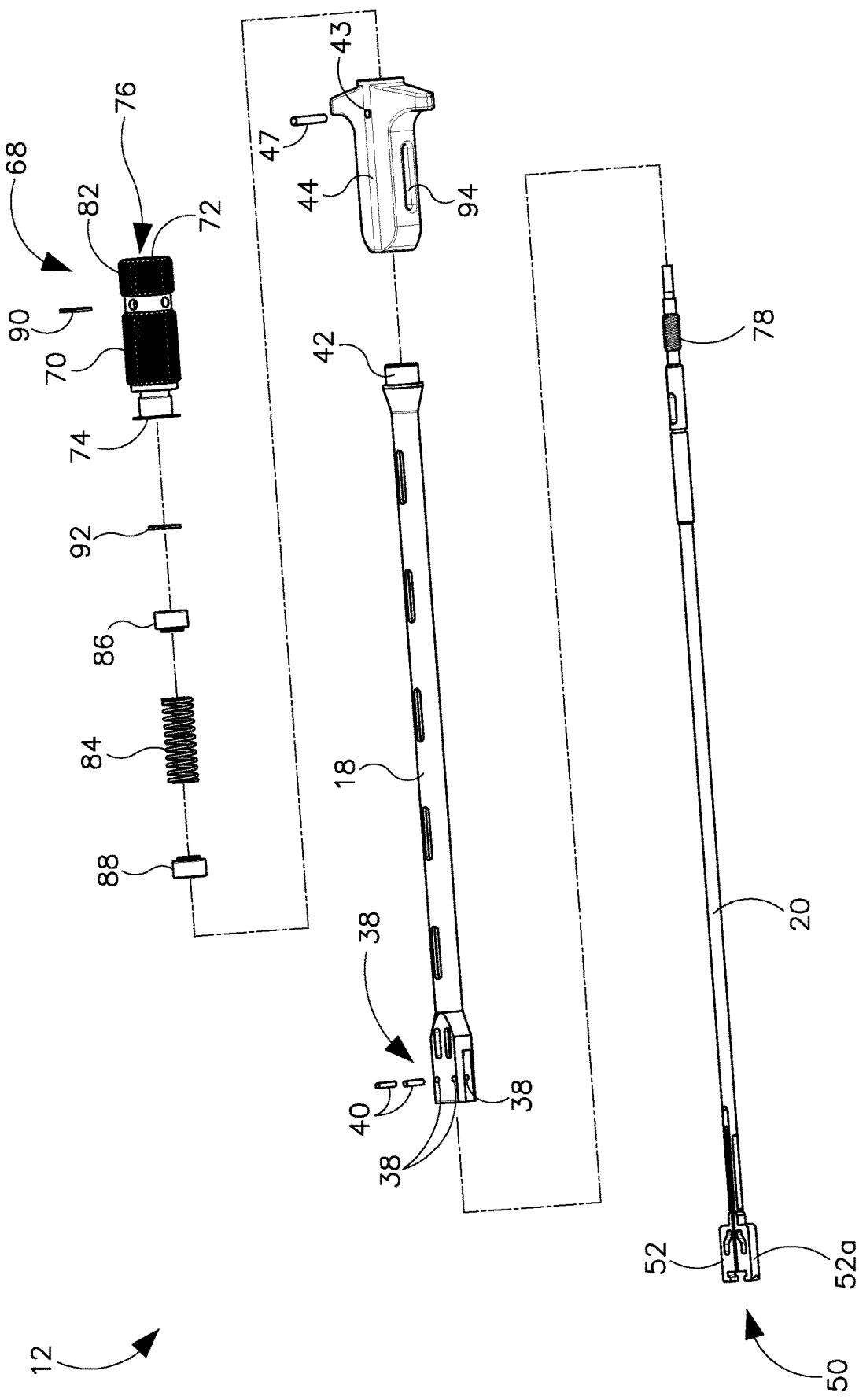
FIG. 3 is a perspective view of the components shown in FIG. 1 with parts separated.
Figure 4:
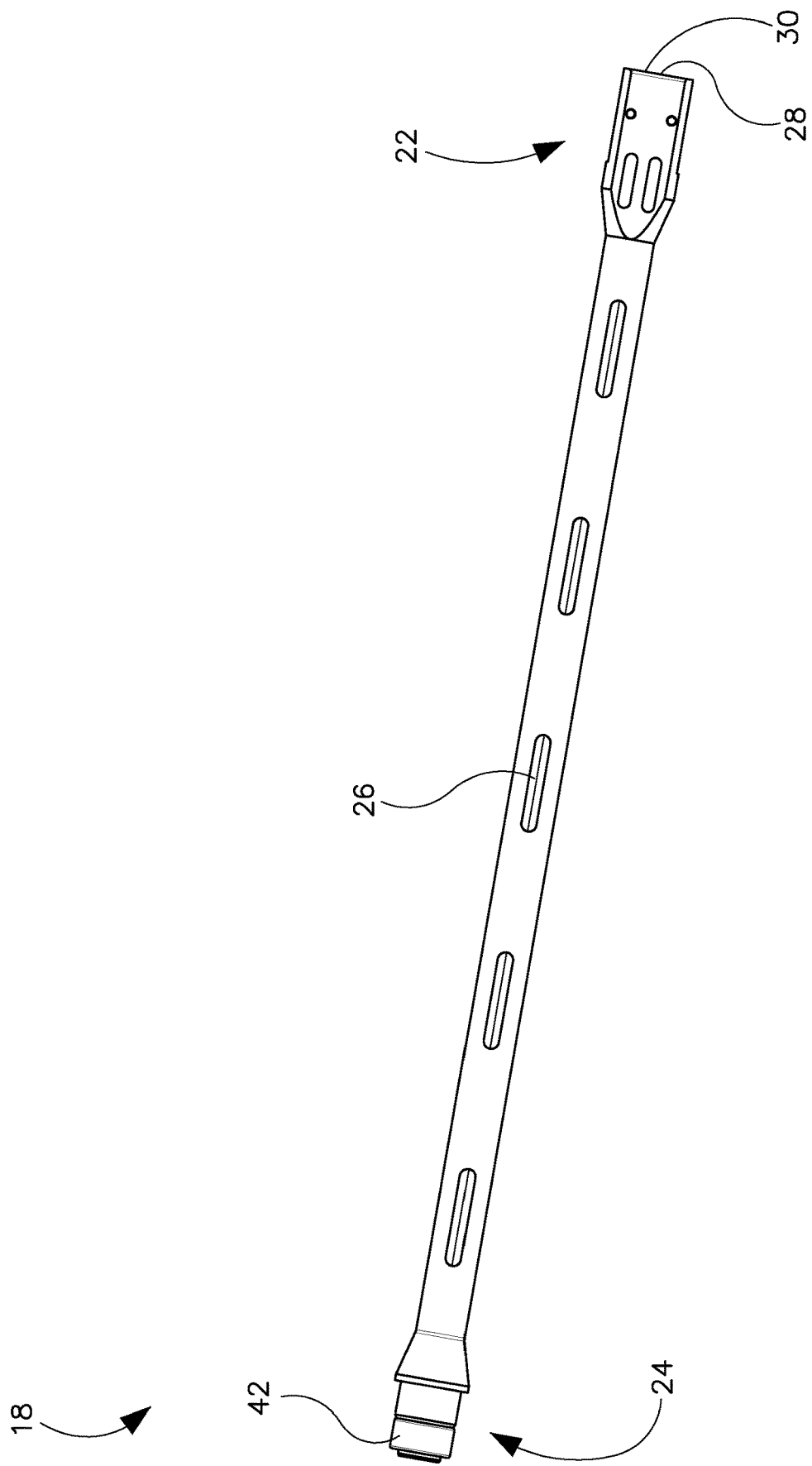
FIG. 4 is a perspective view of components shown in FIG. 1.

Plate holder 12 is configured for connecting to an implant, for example, a lamina plate 100, as shown in FIG. 1 and described herein. In some embodiments, plate 100 is provisionally secured to plate holder 12 and is configured to facilitate plate 100 manipulation within a surgical site, for example, within a section of a spine. Plate holder 12 extends between an end 14 and an end 16. Plate holder 12 includes a member, for example, an outer tube 18 that defines an axis, for example, a longitudinal axis AA, as shown in FIG. 1. Outer tube 18 is configured for engagement with a member, for example, an inner shaft 20, as shown in FIG. 3, such that inner shaft 20 is movable relative to outer tube 18 between a retracted position and an extended position, as described herein. Outer tube 18 extends between an end 22 and an end 24, as shown in FIG. 4. In some embodiments, outer tube 18 may have various cross-section configurations, for example, cylindrical, oval, oblong, triangular, rectangular, square, polygonal, irregular, uniform, non-uniform, variable and/or tapered. In some embodiments, outer tube 18 may have various surface configurations, for example, rough, threaded for connection with surgical instruments, arcuate, undulating, porous, semi-porous, dimpled, polished and/or textured.

Outer tube 18 defines an inner surface 26 configured for disposal of inner shaft 20, as shown in FIG. 4. In some embodiments, inner surface 26 may have various surface configurations, for example, rough, threaded for connection with surgical instruments, arcuate, undulating, porous, semi-porous, dimpled, polished and/or textured.

Figure 5:
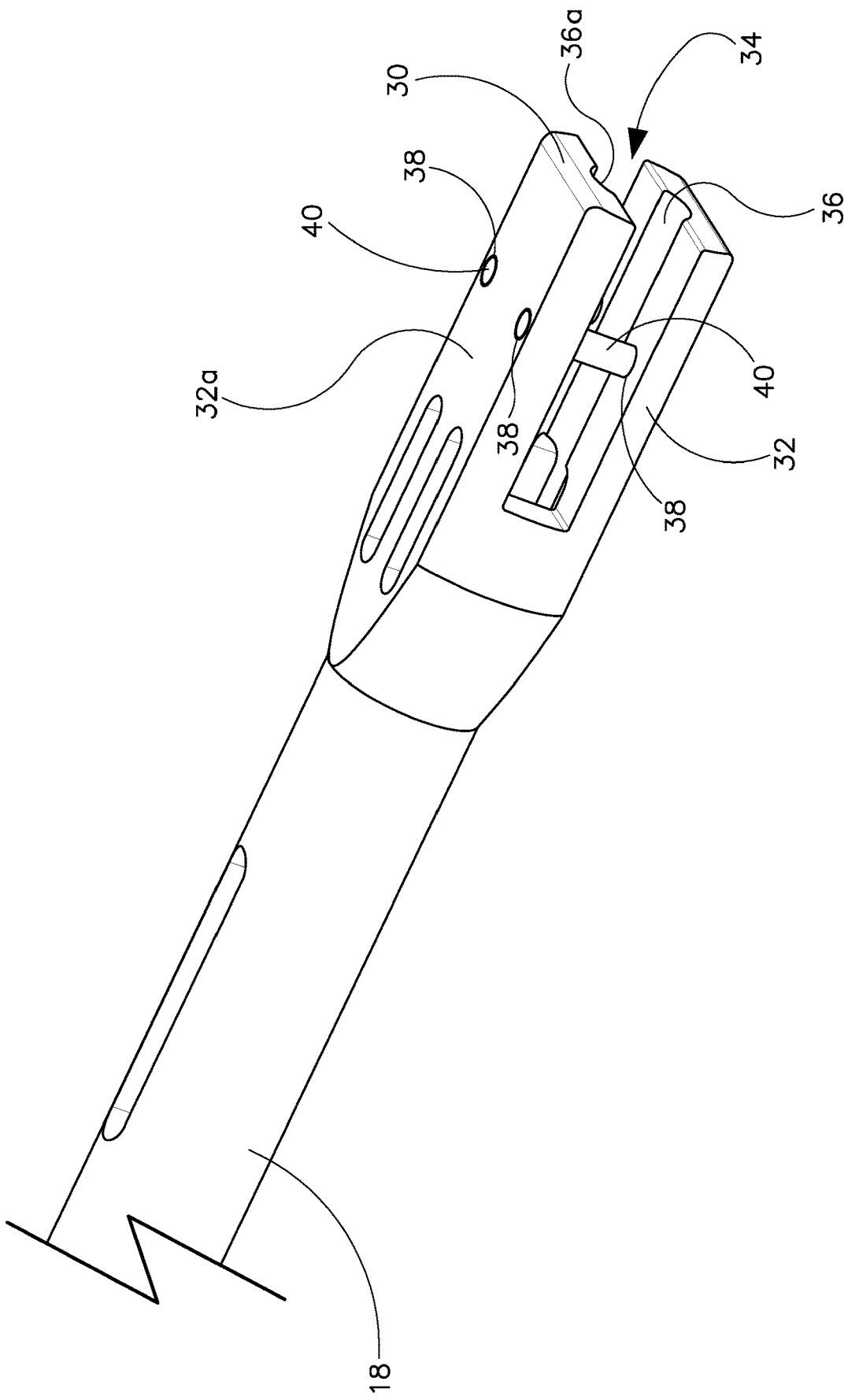
FIG. 5 is a break away view of components shown in FIG. 1.

At end 22, outer tube 18 includes a distal surface 28, as shown in FIG. 4. Distal surface 28 includes an even configuration comprising a straight tip 30, as shown in FIG. 5. Tip 30 is configured for engagement with a surface of implant 100, as described herein. Tip 30 includes a set of arms 32, 32a, as shown in FIG. 5. An inner surface of arms 32, 32a defines a cavity 34 configured for disposal with an end 46 of inner shaft 20, as described herein. An inner surface of each arm 32, 32a defines channels 36, 36a respectively. Channels 36, 36a are configured for slidable engagement with end 46 of inner shaft 20, during translation of inner shaft 20, as described herein. In some embodiments, channels 36, 36a may have various surface configurations, for example, rough, arcuate, undulating, porous, semi-porous, dimpled, polished and/or textured.

A surface of each arm 32, 32a includes openings 38, as shown in FIGS. 3 and 5. Openings 38 are configured for disposal with a guide element, including a projection, for example, a splay pin 40. As shown in FIG. 3, plate holder 12 includes a pair of splay pins 40. Splay pins 40 are configured for translation with a portion of end 46 of inner shaft 20, as described herein. In some embodiments, splay pins 40 are alternatively configured and include dowel pins, spring pins, taper pins, headed pins, quick release pins and/or locking pins.

End 24 includes a surface 42 configured for engagement with a handle, for example, a tee handle 44, as shown in FIG. 3. Handle 44 is configured for engagement with a user. In some embodiments, handle 44 may have various configurations, for example, undulating, irregular, non-uniform, variable and/or tapered. In some embodiments, handle 44 may have various cross-section configurations, such as, for example, cylindrical, oval, oblong, triangular, rectangular, square, polygonal, irregular, uniform, non-uniform, variable and/or tapered. In some embodiments, handle 44 includes a gripping surface configured to facilitate maneuvering of plate holder 12. In some embodiments, all or only a portion of the gripping surface may have alternate surface configurations, such as, for example, rough, threaded for connection with surgical instruments, arcuate, undulating, porous, semi-porous, dimpled, polished and/or textured according to facilitate gripping.

Inner shaft 20 extends between end 46 and an end 48. In some embodiments, inner shaft 20 may have various cross-section configurations, for example, cylindrical, oval, oblong, triangular, rectangular, square, polygonal, irregular, uniform, non-uniform, variable and/or tapered. In some embodiments, inner shaft 20 may have various surface configurations, for example, rough, threaded for connection with surgical instruments, arcuate, undulating, porous, semi-porous, dimpled, polished and/or textured.

Figure 6:
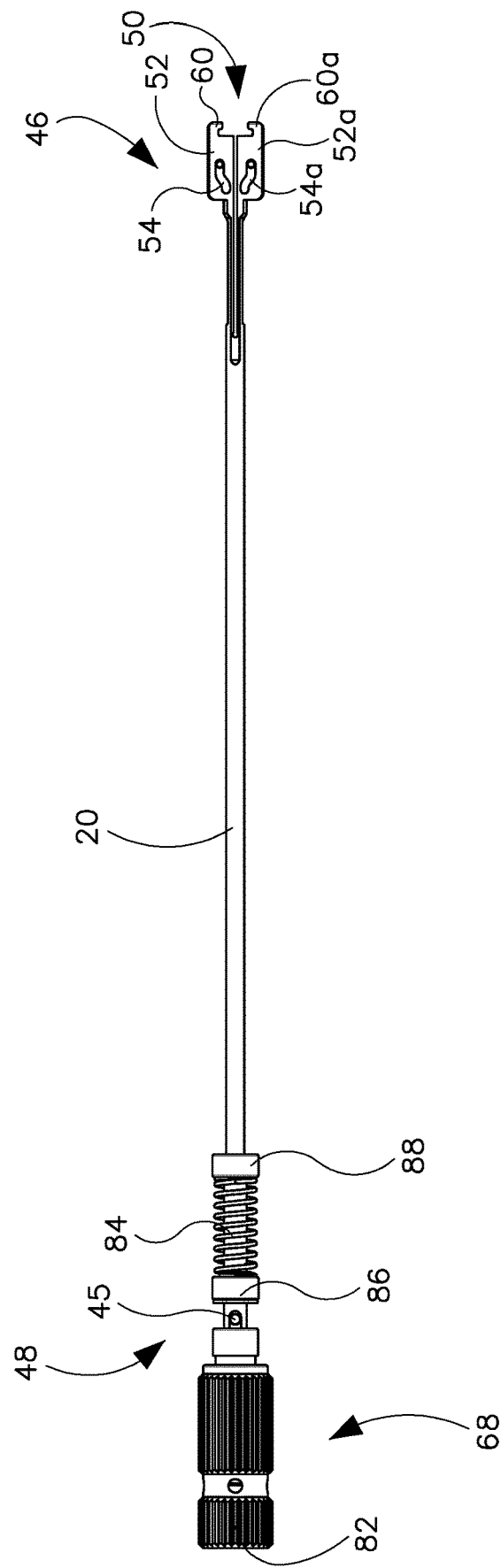
FIG. 6 is a side view of components shown in FIG. 1.

End 48 is configured for engagement with handle 44 via an opening 43 of handle 44, a slot 45 of end 48 and a pin 47, as shown in FIGS. 3 and 6. End 46 includes a capture member, for example, a capture element 50 including a pair of arms 52, 52a, as shown in FIGS. 6 and 8. Arms 52, 52a are axially translatable relative to outer tube 18 via an actuator 68 and are configured for disposal in a position, for example, an open position and/or a closed position, as described herein. In some embodiments, arms 52, 52a may have various cross-section configurations, for example, cylindrical, oval, oblong, triangular, rectangular, square, polygonal, irregular, uniform, non-uniform, variable and/or tapered. In some embodiments, arms 52, 52a may have various surface configurations, for example, rough, threaded for connection with surgical instruments, arcuate, undulating, porous, semi-porous, dimpled, polished and/or textured.

Arms 52, 52a include a surface that define a slot 54 and a slot 54a respectively, as shown in FIG. 8. Slots 54, 54a are configured for engagement with pins 40. Slots 54, 54a extend between a proximal end 56, 56a and distal end 58, 58a respectively. A knob, for example, a turn knob 70 of actuator 68 is rotated to move pins 40 along slots 54, 54a, as described herein. Pins 40 engage ends 56, 56a in the open position such that arms 52, 52a are configured to receive plate 100, and pins 40 engage ends 58, 58a in the closed position such that arms 52, 52a are configured to engage and capture plate 100, as described herein. Slots 54, 54a are elongated and angled. In some embodiments, slots 54, 54a may have various configurations, for example, irregular, uniform, non-uniform, variable, angled, straight and/or tapered.

Arms 52, 52a include tangs 60, 60a respectively, as shown in FIGS. 6-8. Tangs 60, 60a are configured for capturing plate 100. Tangs 60, 60a are axially translatable relative to inner shaft 20, as shown in FIG. 7. A surface of each tang 60, 60a defines a curved tip 62, 62a respectively. Tips 62, 62a are configured to engage plate 100 at varying orientations on plate 100. In some embodiments, tips 62, 62a may have various configurations, for example, irregular, uniform, non-uniform, variable and/or tapered. In some embodiments, tips 62, 62a may have various surface configurations, for example, rough, arcuate, undulating, porous, semi-porous, dimpled, polished and/or textured.

Figure 12:
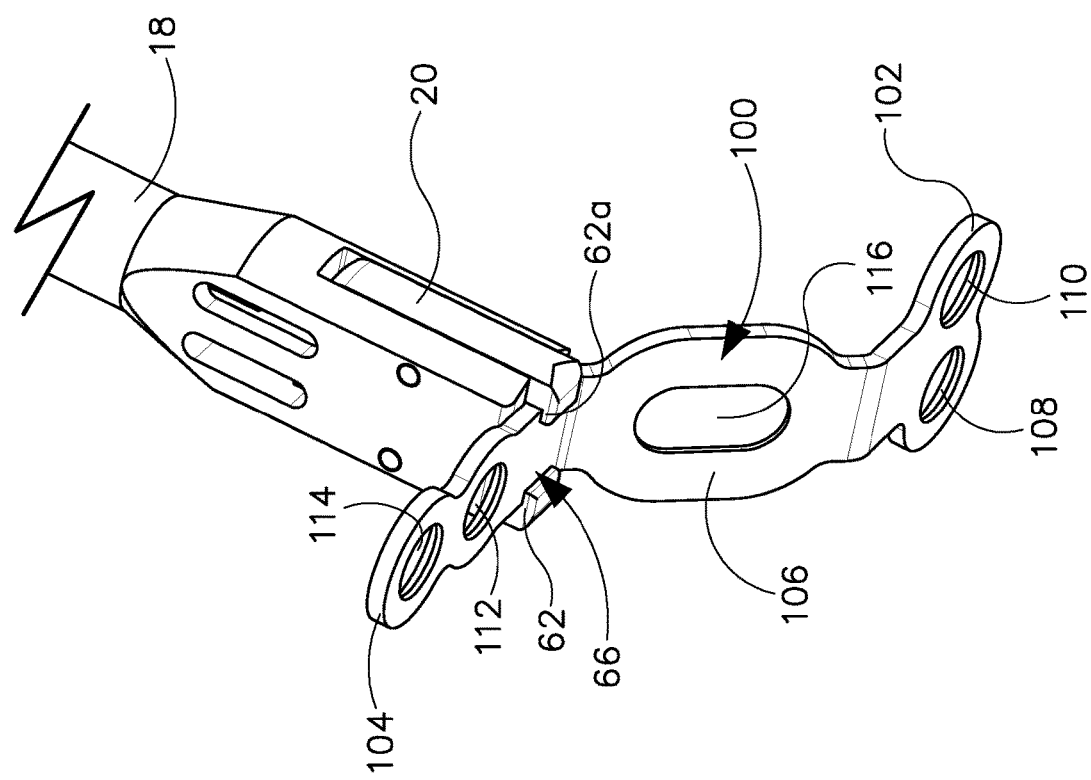
FIG. 12 is a break away view of components shown in FIG. 1.

Tangs 60, 60a include engagement surfaces 64, 64a respectively and surfaces of tangs 60, 60a define a cavity 66 configured for disposal of plate 100, as shown in FIGS. 8 and 12. In some embodiments, all or only a portion of surfaces 64, 64a may have alternate surface configurations, such as, for example, planar, rough, undulating, porous, semi-porous, dimpled, polished and/or textured to facilitate capture of plate 100.

Figure 2:
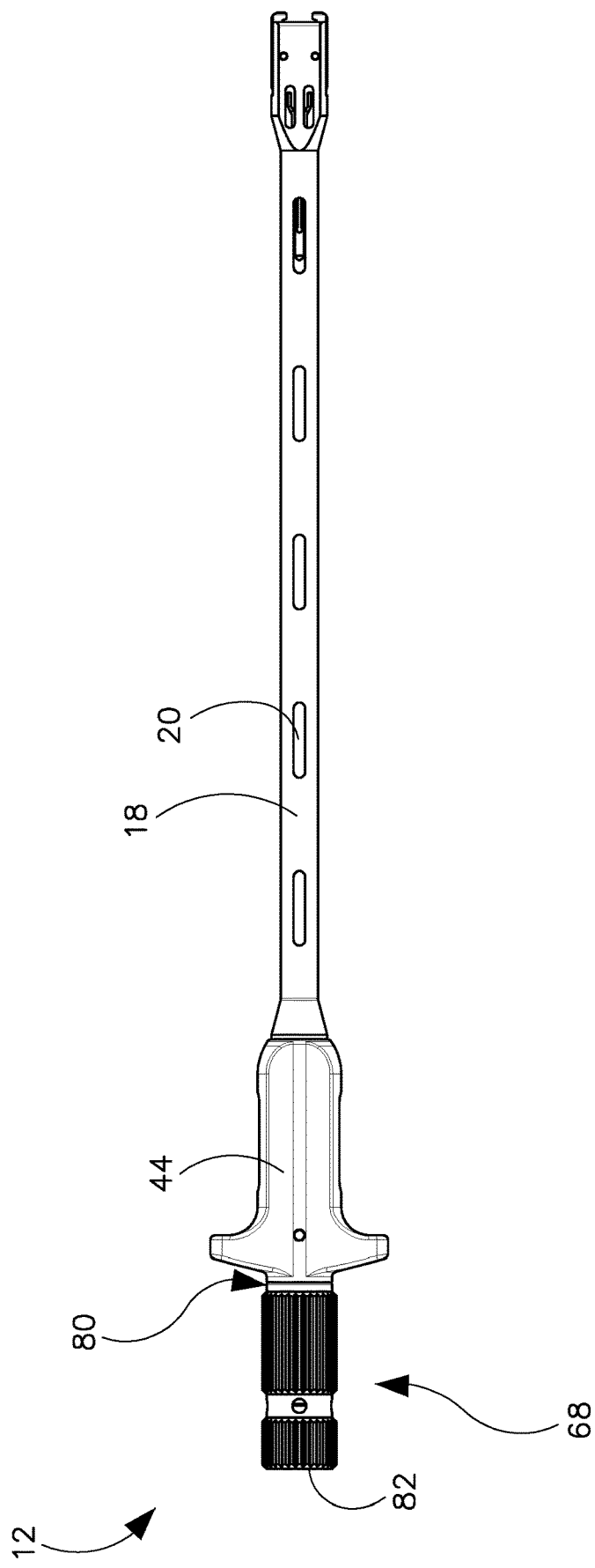
FIG. 2 is a side view of the components shown in FIG. 1.

Plate holder 12 includes actuator 68, as shown in FIGS. 2 and 3. Actuator 68 is configured to move inner shaft 20 relative to outer tube 18 between the retracted position and the extended position, as described herein. As described herein, actuator 68 includes knob 70, as shown in FIG. 3. Knob 70 is configured for rotation and axial translation relative to outer tube 18. Knob 70 includes an end 72 and an end 74, as shown in FIG. 3. End 74 is configured for disposal with handle 44, as shown in FIG. 2. An outer surface of knob 70 includes a gripping surface configured to facilitate maneuvering of knob 70. In some embodiments, all or only a portion of the gripping surface may have alternate surface configurations, such as, for example, rough, threaded for connection with surgical instruments, arcuate, undulating, porous, semi-porous, dimpled, polished and/or textured according to facilitate gripping.

Figure 9:
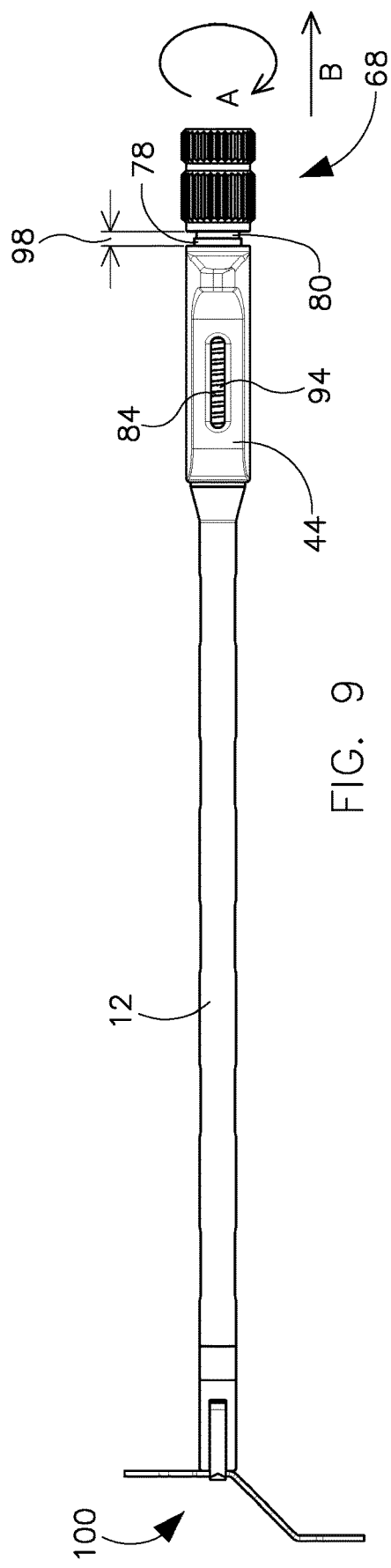
FIG. 9 is a side view of components shown in FIG. 1.

Knob 70 includes a threaded inner surface 76 configured for engagement with a threaded outer surface 78 at end 48 of inner shaft 20, as shown in FIG. 3. Threaded engagement of surfaces 76 and 78 form a lock 80, as shown in FIGS. 2 and 9. Lock 80 is configured to selectively fix inner shaft 20 in the retracted position or the extended position, as described herein.

End 72 includes a button, for example, a push button 82, as shown in FIG. 3. Button 82 is translatable relative to outer tube 18 to overcome a bias, for example, a spring 84 such that inner shaft 20 is movable between the retracted position and the extended position. Spring 84 is configured for disposal within handle 44 and is disposed about a portion of end 48 of inner shaft 20 to bias inner shaft 20 and to position inner shaft 20 in the retracted position, as shown in FIGS. 6 and 8. Spring caps 86, 88 are disposed at ends of spring 84 and are disposed about a portion of end 48 of inner shaft 20, as shown in FIGS. 3 and 6. Retaining clips 90, 92 are disposed between knob 70 and button 82 and between end 74 and retaining clip 86, respectively, as shown in FIG. 3.

Figure 10:
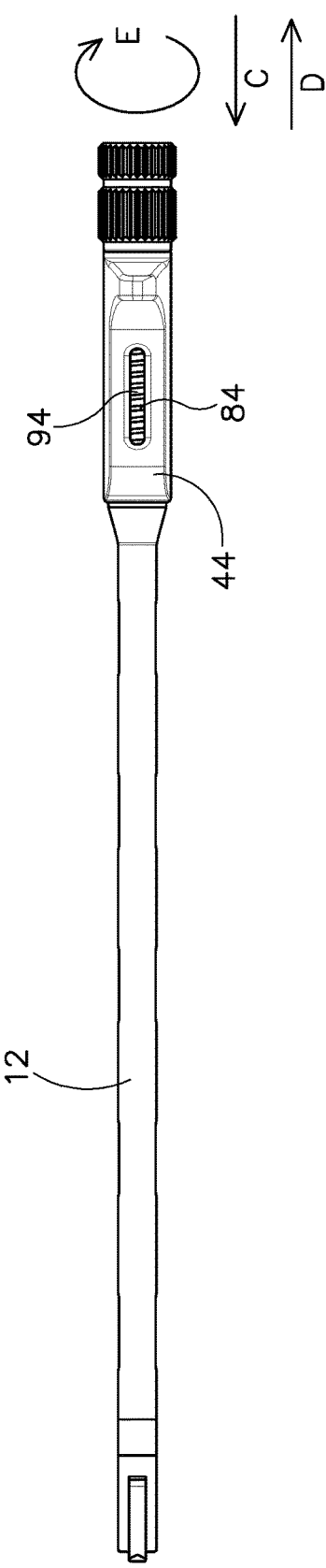
FIG. 10 is a side view of components shown in FIG. 1.

A window 94 is defined from a surface of handle 44, as shown in FIGS. 3, 9 and 10. Window 94 is configured to facilitate viewing of spring 84 for example, during the retracted position and extended position of inner shaft 20, as shown in FIGS. 9 and 10. In some embodiments, window 94 may have various configurations, including, for example, oval, oblong, triangular, rectangular, square, polygonal, irregular, uniform, non-uniform, variable and/or tapered.

Figure 13:
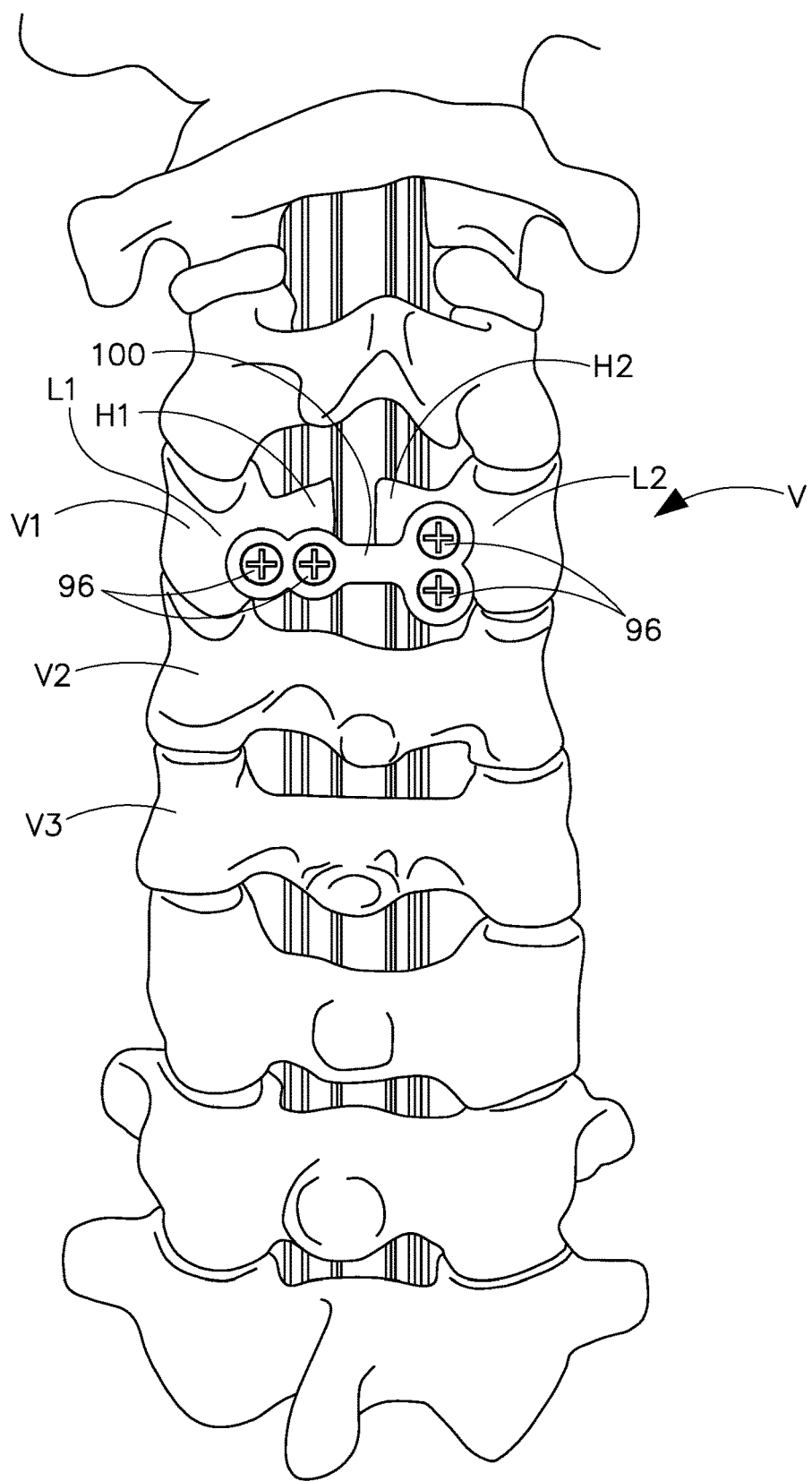
FIG. 13 is a plan view of components shown in FIG. 1 disposed with vertebrae.

As described herein, plate 100 includes a lamina plate, as shown in FIGS. 1, 9 and 12. Plate 100 is configured for use in medical procedures, for example, laminoplasty procedures. Plate 100 is configured for fixation with laminae via one or more fixation elements, for example, bone fasteners 96, as shown in FIG. 13. In some embodiments, plate 100 is configured for stabilizing vertebral tissue, such as, for example, divided and/or separated lamina, transverse process, pars interarticularis, facet or spinous process portions of one or more vertebral levels. In some embodiments, plate 100 is configured for stabilizing one or more vertebral levels via attachment with a vertebral level having removed, non-separated portions of vertebral tissue, such as, for example, a lamina, transverse process, pars interarticularis, facet or spinous process, for example, such that a cavity, relief or notch is created in the vertebral tissue.

Plate 100 extends between an end 102 and an end 104, as shown in FIG. 12. Ends 102, 104 are configured for engagement with tissue, for example, lamina tissue. An intermediate portion 106 is disposed between ends 102 and 104. End 102, end 104 and portion 106 are angled relative to each other, as shown in FIG. 12. A surface of end 102 defines openings 108, 110 configured for disposal of bone fasteners 96. A surface of end 104 defines openings 112, 114 configured for disposal of bone fasteners 96. A surface of portion 106 defines an opening 116. Opening 116 is configured for disposal and/or engagement with a bone fastener 96 and/or one or more surgical tools. In some embodiments, plate 100 may have various cross-section configurations, for example, cylindrical, oval, oblong, triangular, rectangular, square, polygonal, irregular, uniform, non-uniform, variable and/or tapered. In some embodiments, outer plate 100 may have various surface configurations, for example, rough, threaded for connection with surgical instruments, arcuate, undulating, porous, semi-porous, dimpled, polished and/or textured.

Figure 11:
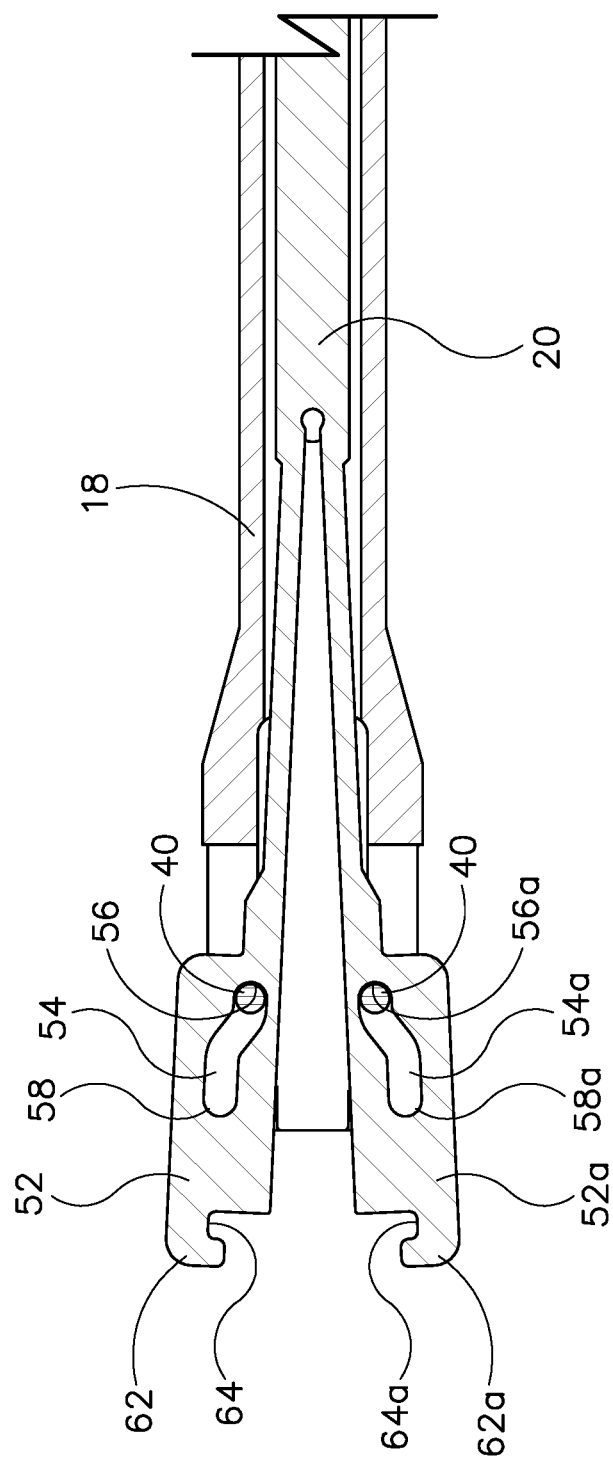
FIG. 11 is a beak away cross sectional view of components shown in FIG. 10.

To capture plate 100 with plate holder 12, a user positions plate 100 adjacent end 14. Inner shaft 20 is disposed in a retracted position due to force applied via spring 84 disposed about inner shaft 20. Arms 52, 52*a* are disposed in a position, for example, a closed position, as shown in FIG. 8. In some embodiments, the closed position corresponds to the retracted position. Knob 70 is rotated in a direction, as shown by arrow A in FIG. 9, to translate knob 70 away from handle 44 in a direction, as shown by arrow B in FIG. 9. A gap 98 is formed between handle 44 and knob 70, exposing a portion of thread 78 of outer sleeve 20, as shown in FIG. 9. Button 82 is depressed in a direction, as shown by arrow C in FIG. 10, to overcome the force applied via spring 84 on inner shaft 20 to translate inner shaft 20 in the direction of arrow C, positioning outer shaft 20 into the extended position as pins 40 move in slots 54, 54*a*. Pins 40 move from ends 58, 58*a* to ends 56, 56*a*, as shown in FIGS. 8 and 11. Arms 52, 52*a* are outwardly radially movable relative to axis AA for disposal in a position, for example, an open position, as shown in FIG. 11 to receive plate 100. In some embodiments, the open position corresponds to the extended position.

Plate 100 contacts surfaces 64, 64*a* of tangs 60, 60*a*. In some embodiments, plate holder 12 is configured to engage plate 100 at varying orientations on plate 100. In some embodiments, plate holder 12 is configured to engage plate 100 at a center, including intermediate portion 106 of plate 100. To provisionally capture plate 100 with plate holder 12, button 82 is released, translating inner shaft 20 in a direction, as shown by arrow D in FIG. 10, positioning outer shaft 20 into the retracted position as pins 40 move in slots 54, 54*a*. Pins 40 move from ends 56, 56*a* to ends 58, 58*a*, as shown in FIGS. 8 and 11. Arms 52, 52*a* are inwardly radially movable relative to axis AA for disposal in the closed position, as shown in FIG. 8, to engage and provisionally capture plate 100 with tangs 60, 60*a*. Plate 100 is provisionally captured with tangs 60, 60*a* such that the user can easily secure plate 100 with plate holder 12. Knob 70 is rotated in a direction, as shown by arrow E in FIG. 10, to compress and fix plate 100 to plate holder 12 via lock 80.

In assembly, operation and use, surgical system 10, similar to the systems and methods described herein, is employed to treat a selected section of vertebrae V. A medical practitioner obtains access to a surgical site including vertebrae in any appropriate manner, such as through incision and retraction of tissues. In some embodiments, surgical system 10 can be used in any existing surgical method or technique including open surgery, mini-open surgery, minimally invasive surgery and percutaneous surgical implantation, whereby vertebrae is accessed through a mini-incision, or sleeve that provides a protected passageway to the area. Once access to the surgical site is obtained, the particular surgical procedure can be performed for treating the spine disorder. In some embodiments, one or all of the components of surgical system 10 can be delivered or implanted as a pre-assembled device or can be assembled in situ. The components of surgical system 10 may be completely or partially revised, removed or replaced.

An incision is made in the body of a patient and a cutting instrument (not shown) creates a surgical pathway for implantation of components of surgical system 10 with a portion of vertebrae, for example, lamina L1 and L2 of vertebrae, as shown in FIG. 13. A preparation instrument (not shown) can be employed to prepare tissue surfaces of vertebrae, as well as for aspiration and irrigation of a surgical region. For example, a cutting instrument (not shown) can be employed to engage a spinous process (not shown-removed) of vertebral level V1, as shown in FIG. 13. The spinous process is removed with the cutting instrument to form a cavity, gap or space between lamina L1 and lamina L2. A relief is cut down a medial cortical layer of lamina L1 to create a bone hinge H1. A relief is cut down the medial cortical layer of lamina L2 to create a bone hinge H2. In some embodiments, reliefs can include a groove, gutter or trough, and can be formed using a high-speed burr drill.

Plate holder 12, similar to that described herein, is connected with plate 100 and/or bone fasteners 96 for orientation and delivery of plate 100 along the surgical pathway and fixation with surfaces of lamina L1 and L2, as shown in FIG. 13. Plate holder 12 introduces the components of surgical system 10 along the surgical pathway to implant plate 100 and/or bone fasteners 96 in substantial alignment to attach plate 100 and/or bone fasteners 96 with surfaces of lamina L1 and L2.

To capture plate 100 with plate holder 12, a user positions plate 100 adjacent end 14. Inner shaft 20 is disposed in a retracted position. Arms 52, 52*a* are disposed in a closed position, as shown in FIG. 8. Knob 70 is rotated in a direction, as shown by arrow A in FIG. 9, to translate knob 70 away from handle 44 in a direction, as shown by arrow B in FIG. 9. Gap 98 forms between handle 44 and knob 70, exposing a portion of thread 78 of outer sleeve 20. Button 82 is depressed in a direction, as shown by arrow C in FIG. 10, to overcome the force applied via spring 84 on inner shaft 20 to translate inner shaft 20, in the direction of arrow C, positioning outer shaft 20 into the extended position as pins 40 move in slots 54, 54*a*. Pins 40 move from ends 58, 58*a* to ends 56, 56*a*, as shown in FIGS. 8 and 11. Arms 52, 52*a* are outwardly radially movable relative to axis AA for disposal in an open position, as shown in FIG. 11 to receive plate 100.

Plate 100 contacts surfaces 64, 64*a*, as shown in FIGS. 11 and 12. To provisionally capture plate 100 with plate holder 12, button 82 is released, translating inner shaft 20 in a direction, as shown by arrow D in FIG. 10, positioning outer shaft 20 into the retracted position as pins 40 move in slots 54, 54*a*. Pins 40 move from ends 56, 56*a* to ends 58, 58*a*, as shown in FIGS. 8 and 11. Arms 52, 52*a* are inwardly radially movable relative to axis AA for disposal in the closed position, as shown in FIG. 8, to engage and provisionally capture plate 100 with tangs 60, 60*a*. Plate 100 is provisionally captured with tangs 60, 60*a* such that the user can easily secure plate 100 with plate holder 12. Knob 70 is rotated in a direction, as shown by arrow E in FIG. 10, to compress and fix plate 100 to plate holder 12 via lock 80. Plate 100 is delivered to the surgical site, for example, in between adjacent lamina L1 and L2, and bone fasteners 96 are disposed within openings 108, 110, 112 and 114 to fix plate 100 to the surfaces of lamina L1 and L2, as shown in FIG. 13. To release plate 100 from plate holder 12, plate holder 12 is oriented in the extended position and open position, as described above.

Upon completion of the procedure, the surgical instruments, assemblies and non-implanted components of surgical system 10 are removed and the incision is closed. Surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

In some embodiments, the bone fasteners may be engaged with tissue in various orientations, such as, for example, series, parallel, offset, staggered and/or alternate vertebral levels. In some embodiments, one or more of the one fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

Figure 14:
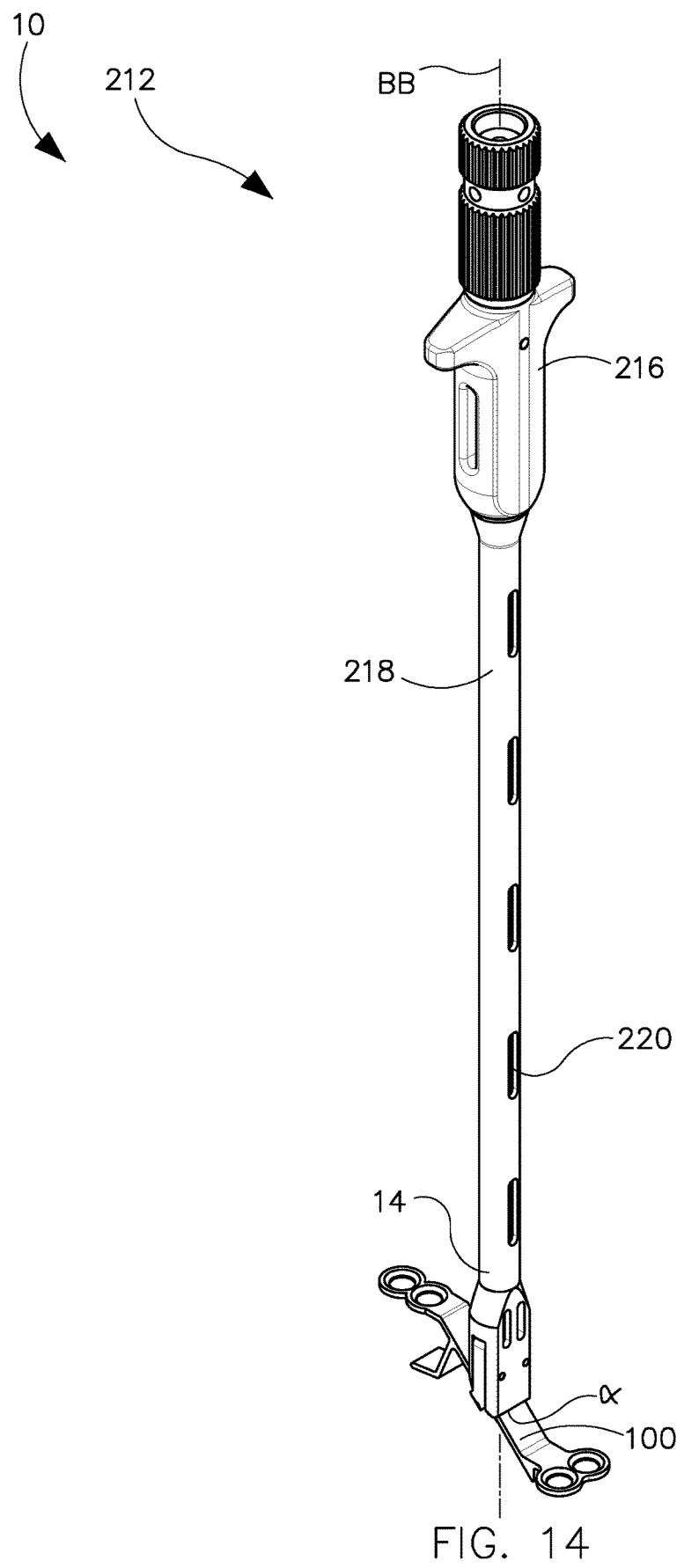
FIG. 14 is a perspective view of components of one embodiment of a surgical system in accordance with the principles of the present disclosure.
Figure 15:
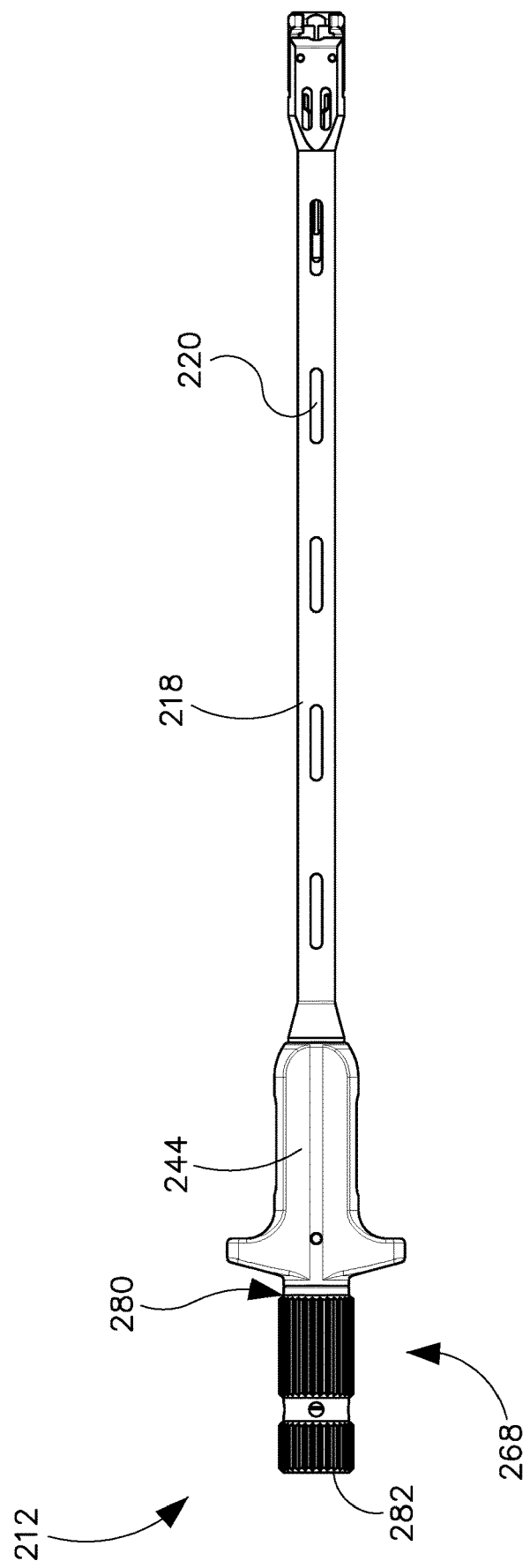
FIG. 15 is a side view of components shown in FIG. 14.
Figure 16:
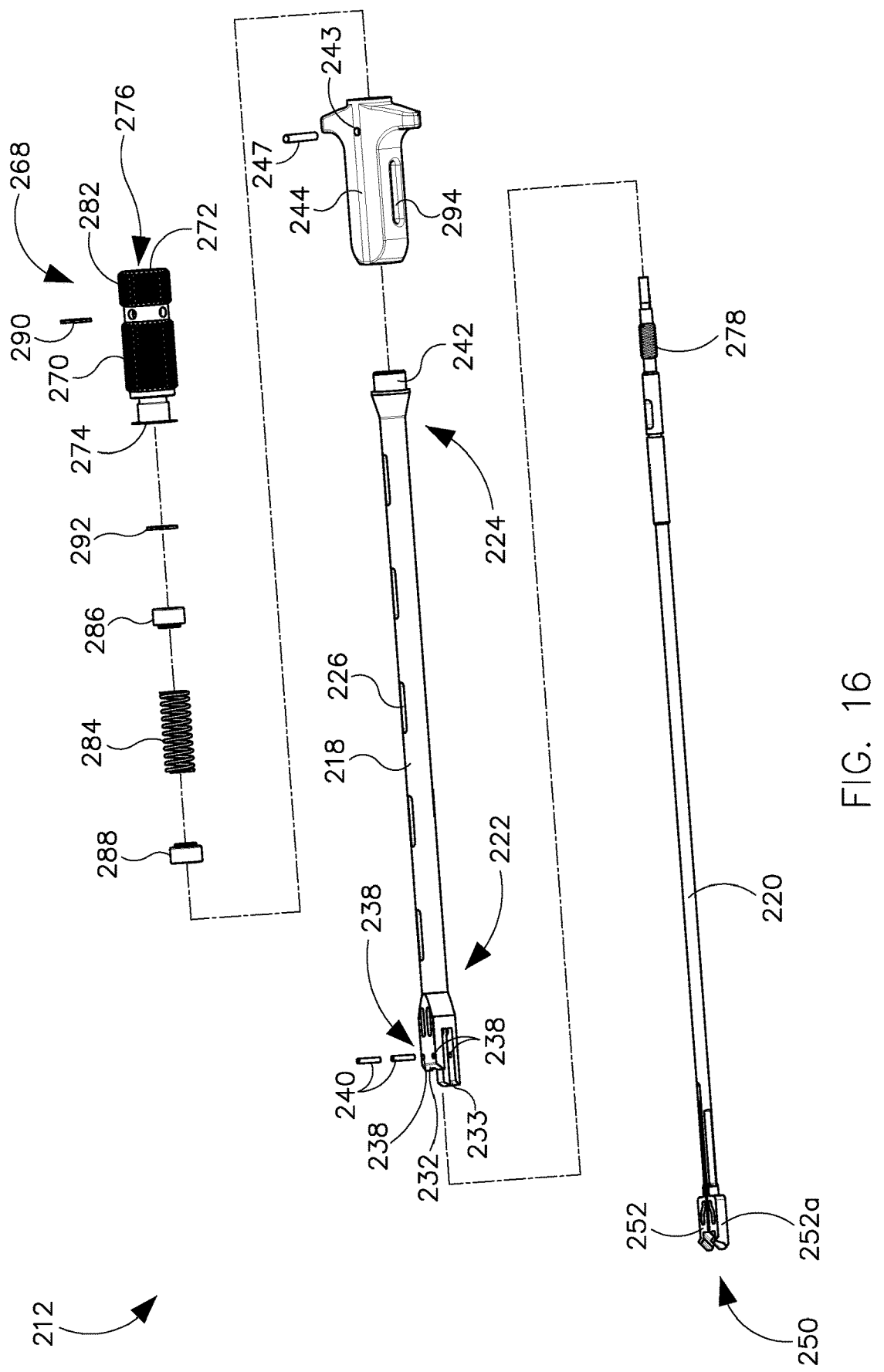
FIG. 16 is a perspective view of the components shown in FIG. 14 with parts separated.

In one embodiment, as shown in FIG. 14-20, surgical system 10, similar to the system and method described above with regard to FIGS. 1-13, includes a plate holder 212, similar to plate holder 12, as described herein. Plate holder 212 extends between an end 214 and an end 216. Plate holder 212 includes a member, for example, an outer tube 218, similar to outer tube 18, as described herein, that defines an axis, for example, a longitudinal axis BB, as shown in FIG. 14. Outer tube 218 is configured for engagement with a member, for example, an inner shaft 220, as shown in FIG. 15, similar to shaft 20, as described herein, such that inner shaft 220 is movable relative to outer tube 218 between a retracted position and an extended position. Outer tube 218 extends between an end 222 and an end 224, as shown in FIG. 16. Outer tube 218 defines an inner surface 226 configured for disposal of inner shaft 220, as shown in FIG. 16.

Figure 17:
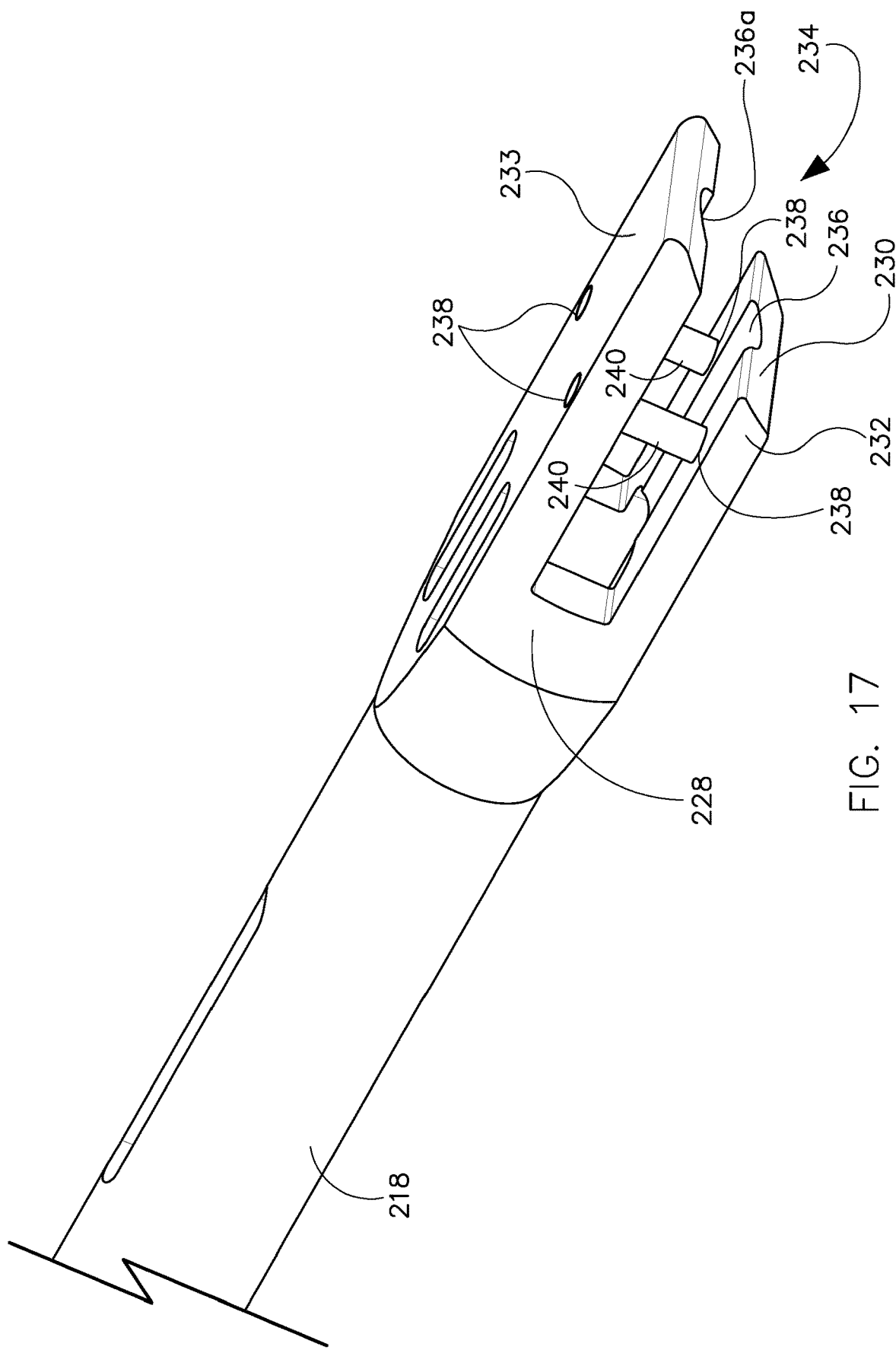
FIG. 17 is a break away view of components shown in FIG. 14.

At end 222, outer tube 218 includes a distal surface 228, as shown in FIG. 17. Distal surface 228 includes an angled surface relative to axis BB comprising an angled tip 230, as shown in FIGS. 16 and 17. Tip 230 is configured for engagement with a surface of implant 100, similar to tip 30, as described herein. Tip 230 includes a set of arms 232, 233, as shown in FIGS. 16 and 17. Arm 233 includes a length that is longer than a length of arm 232, as shown in FIG. 16. An inner surface of arms 232, 233 defines a cavity 234 configured for disposal with an end 246 of inner shaft 220, as described herein. An inner surface of each arm 232, 233 defines a channel 236, 236a respectively, as shown in FIG. 17. Channels 236, 236a are configured for slidable engagement with end 246 of inner shaft 220, during translation of inner shaft 220, as described herein.

A surface of each arm 232, 233 includes openings 238, as shown in FIGS. 16 and 17. Openings 238 are configured for disposal with a guide element, including a projection, for example, a splay pin 240. As shown in FIG. 16, plate holder 212 includes a pair of splay pins 240. Splay pins 240 are configured for translation with a portion of end 246 of inner shaft 220, as described herein.

End 224 includes a surface 242 configured for engagement with a handle, for example, a tee handle 244, as shown in FIG. 16, similar to handle 44, as described herein. Handle 244 is configured for engagement with a user.

Figure 18:
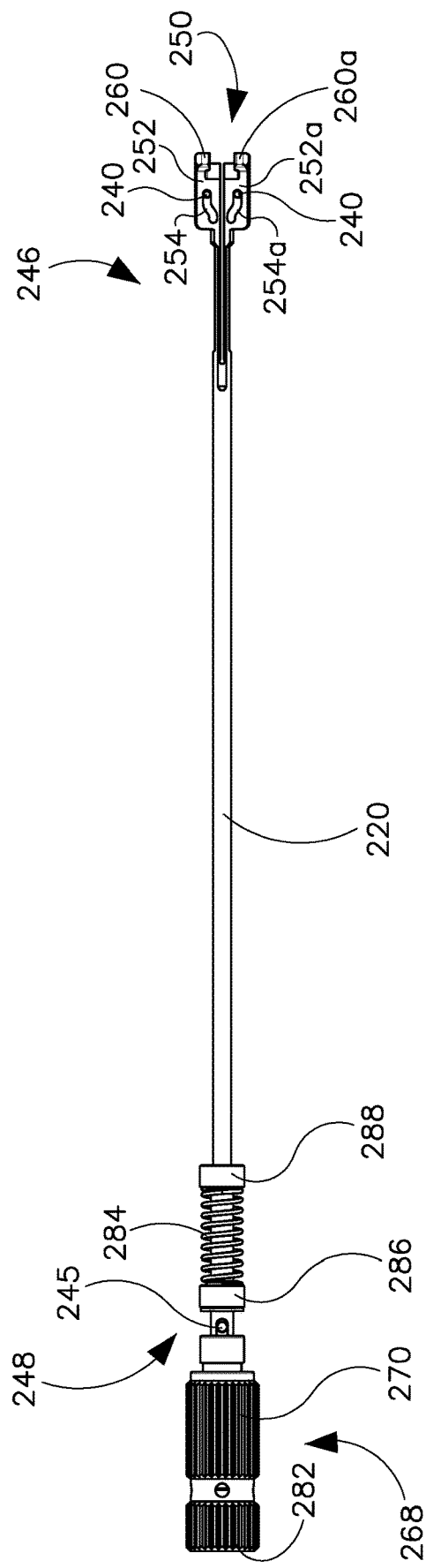
FIG. 18 is a side view of components shown in FIG. 14.
Figure 19:
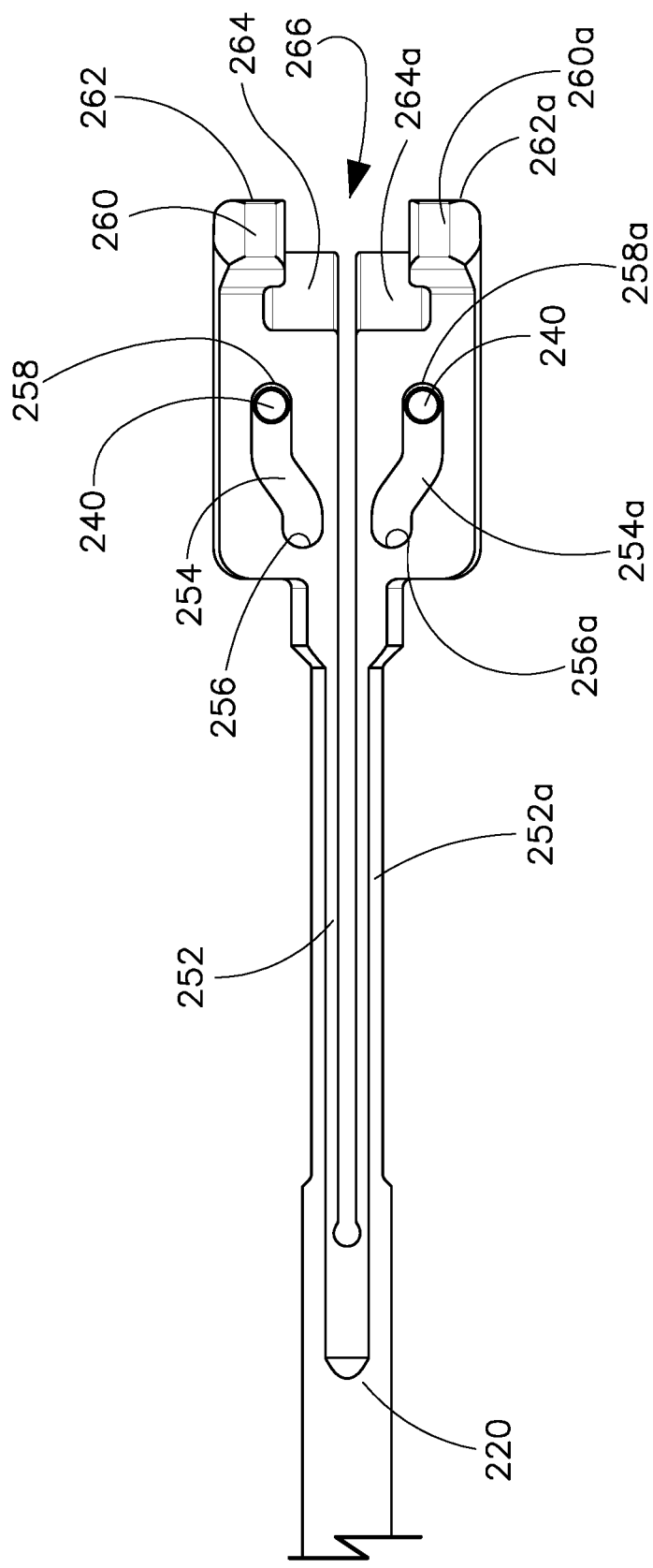
FIG. 19 is a break away view of components shown in FIG. 14.
Figure 20:
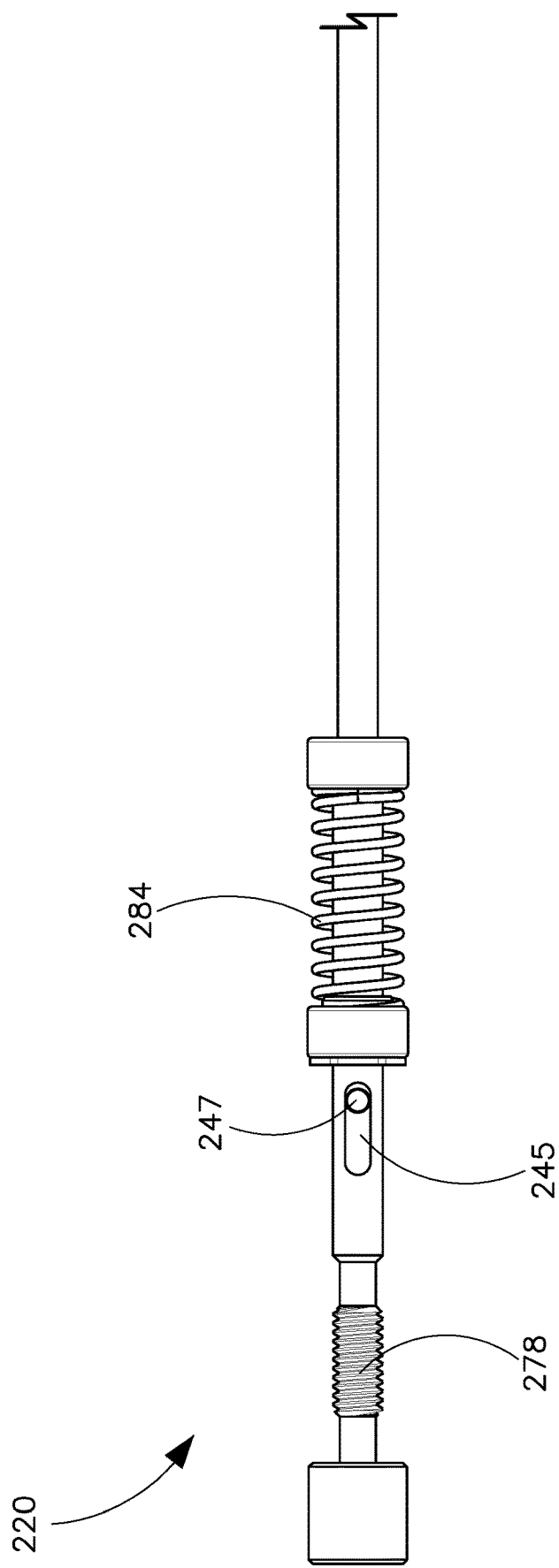
FIG. 20 is a break away view of components shown in FIG. 14.

Inner shaft 220 extends between an end 246 and an end 248. End 248 is configured for engagement with handle 244 via an opening 443 of handle 244, a slot 245 of end 248 and a pin 247, as shown in FIGS. 16, 18 and 20. End 246 includes a capture member, for example, a capture element 250 including a pair of arms 252, 252a, as shown in FIGS. 18 and 19. Arms 252, 252a are axially translatable relative to outer tube 218 via an actuator 268 and are configured for disposal in a position, for example, an open and/or closed position, similar to arms 52, 52a, as described herein.

Arms 252, 252a include a surface that defines a slot 254, 254a respectively, as shown in FIG. 19 and similar to slots 54, 54a, as described herein. Slots 254, 254a are configured for engagement with pin 240. Slots 254, 254a extend between a proximal end 256, 256a and distal end 258, 258a respectively. A knob, for example, a turn knob 270 of actuator 268 is rotated to move pin 240 along slots 254, 254a. Pin 240 engages end 256, 256a in the open position such that arms 252, 252a are configured to receive plate 100, and pin 240 engages end 258, 258a in the closed position such that arms 252, 252a are configured to engage and capture plate 100, as described herein. Slots 254, 254a are elongated and angled. In some embodiments, slots 254, 254a may have various configurations, for example, irregular, uniform, non-uniform, variable, angled, straight and/or tapered.

Arms 252, 252a include tangs 260, 260a respectively, as shown in FIGS. 18 and 19. Tangs 260, 260a are configured for capturing plate 100. Tangs 260, 260a are axially translatable relative to inner shaft 220. A surface of tangs 260, 260a defines angled tips 262, 262a respectively, as shown in FIG. 19. In some embodiments, tips 262, 262a may have various configurations, for example, irregular, uniform, non-uniform, variable and/or tapered. In some embodiments, tips 262, 262a may have various surface configurations, for example, rough, arcuate, undulating, porous, semi-porous, dimpled, polished and/or textured.

Tangs 260, 260a include engagement surfaces 264, 264a respectively and surfaces of tangs 260, 260a define a cavity 266 configured for disposal of plate 100, as shown in FIG. 19. In some embodiments, all or only a portion of surfaces 264, 264a may have alternate surface configurations, such as, for example, planar, rough, undulating, porous, semi-porous, dimpled, polished and/or textured to facilitate capture of plate 100.

Plate holder 212 includes actuator 268, as shown in FIGS. 16 and 18. Actuator 268 is configured to move inner shaft 220 relative to outer tube 218 between the retracted position and the extended position, as described herein. Actuator 268 includes turn knob 270, as shown in FIGS. 16 and 18. Knob 270 is configured for rotation and axial translation relative to outer tube 218. Knob 270 includes an end 272 and an end 274, as shown in FIG. 16. End 274 is configured for disposal with handle 244, as shown in FIGS. 15 and 16. An outer surface of knob 270 includes a gripping surface, similar to the gripping surface disclosed above with regard to knob 70, configured to facilitate maneuvering of knob 270.

Knob 270 includes a threaded inner surface 276 configured for engagement with a threaded outer surface 278 at end 248 of inner shaft 220, as shown in FIG. 16. Threaded engagement of surfaces 276 and 278 form a lock 280, as shown in FIGS. 15 and 16, similar to lock 80, as described herein. Lock 280 is configured to selectively fix inner shaft 220 in the retracted position or the extended position, as described herein.

End 272 includes a button, for example, a push button 282, as shown in FIG. 16. Button 282 is translatable relative to outer tube 218 to overcome a bias, for example, a spring 284 such that inner shaft 220 is movable between the retracted position and the extended position. Spring 284 is configured for disposal within handle 244 and is disposed about a portion of end 248 of inner shaft 220 to bias inner shaft 220 and to position inner shaft 220 in the retracted position. Caps, for example, spring caps 286, 288 are disposed at ends of spring 284 and are disposed about a portion of end 248 of inner shaft 220, as shown in FIGS. 16 and 18. Retaining clips 290, 292 are disposed between knob 270 and button 282 and between end 274 and retaining clip 286, respectively, as shown in FIG. 16.

A window 294 is defined from a surface of handle 244, as shown in FIG. 16. Window 294 is configured to facilitate viewing of spring 284 for example, during the retracted position and extended position of inner shaft 220. In some embodiments, window 294 may have various configurations, including, for example, oval, oblong, triangular, rectangular, square, polygonal, irregular, uniform, non-uniform, variable and/or tapered.

To capture plate 100 with plate holder 212, a user operates plate holder 212 similar to plate holder 12 described herein and the methods described with regard to plate holder 12 described herein. In some embodiments, plate 100 contacts surfaces 264 at an angle α, as shown in FIG. 14. In some embodiments, angle α is 45 degrees. In some embodiments, angle α is in a range of 15 to 90 degrees. In some embodiments, plate holder 212 is configured to engage plate 100 at varying orientations on plate 100. In some embodiments, plate holder 212 is configured to engage plate 100 at a center, including intermediate portion 106 of plate 100.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
    a first member defining a longitudinal axis and including at least one transverse projection;
    a second member having at least one capture element including at least one transverse slot having a proximal end and a distal end,
    the at least one capture element being axially translatable relative to the first member and the at least one transverse projection being movable between the proximal end and the distal end within the at least one transverse slot such that the at least one capture element is outwardly radially movable relative to the longitudinal axis and inwardly radially movable relative to the longitudinal axis to capture a spinal plate.

2. A surgical instrument as recited in claim 1, wherein the first member includes an outer tube defining an inner surface configured for disposal of the second member, the second member including a center shaft.

3. A surgical instrument as recited in claim 1, wherein the first member includes a distal surface having an even configuration comprising a straight tip.

4. A surgical instrument as recited in claim 1, wherein the first member includes an angled surface relative to the axis comprising an angled tip.

5. A surgical instrument as recited in claim 1, wherein the second member is movable relative to the first member between a retracted position and an extended position.

6. A surgical instrument as recited in claim 1, wherein the surgical instrument includes an actuator configured to move the second member relative to the first member between a retracted position and an extended position.

7. A surgical instrument as recited in claim 6, wherein the actuator includes a push button that is translatable relative to the first member to overcome a bias.

8. A surgical instrument as recited in claim 7, wherein the second member is biased to the retracted position.

9. A surgical instrument as recited in claim 6, wherein the actuator includes a lock to selectively fix the second member in the retracted position or the extended position.

10. A surgical instrument as recited in claim 6, wherein the actuator includes a threaded knob.

11. A surgical instrument as recited in claim 1, wherein a proximal portion of the second member includes a spring to bias the second member.

12. A surgical instrument as recited in claim 1, wherein the at least one transverse projection is configured to dispose the at least one capture element between an open position and a closed position for capturing the spinal plate.

13. A surgical instrument as recited in claim 1, wherein the at least one capture element includes a pair of arms, each of the arms including a transverse slot, each of the transverse slots configured for engagement with a projection.

14. A surgical instrument as recited in claim 13, wherein the projection engages a proximal end of the slot in the open position and the projection engages a distal end of the slot in the closed position.

15. A surgical instrument as recited in claim 13, wherein the projection includes a splay pin.

16. A surgical instrument as recited in claim 13, wherein the arms are biased inwardly.

17. A surgical instrument as recited in claim 1, wherein the at least one capture element includes a pair of tangs configured to capture a lamina plate.

18. A surgical instrument comprising:
    an outer tube defining a longitudinal axis and including a pair of transverse projections;
    a center shaft having a pair of tangs and a pair of transverse slots,
    the pair of tangs being axially translatable relative to the center shaft and the projections being movable between proximal and distal ends of the slots such that the pair of tangs are outwardly radially movable relative to the longitudinal axis and the pair of tangs are inwardly radially movable relative to the longitudinal axis to capture a lamina plate.

19. A surgical instrument as recited in claim 18, wherein the center shaft is movable relative to the outer tube between a retracted position and an extended position.

20. A surgical instrument comprising:
a first member defining a longitudinal axis and at least one transverse projection;
a second member including a capture member having at least one transverse slot including a proximal end and a distal end,
the capture member being axially translatable relative to the first member and the at least one transverse projection being movable between the proximal end and the distal end within the at least one transverse slot such that the capture member is expandable and contractible for capturing a spinal plate.

\* \* \* \* \*